United States Patent
Seo et al.

(10) Patent No.: US 10,195,285 B2
(45) Date of Patent: Feb. 5, 2019

(54) AGTR1 APTAMER-ANTICANCER DRUG COMPLEX FOR CANCER CELL CHEMOTHERAPY

(71) Applicant: KOREA UNIVERSITY RESEARCH AND BUSINESS FOUNDATION, Seoul (KR)

(72) Inventors: Jae-Hong Seo, Gwacheon-si (KR); Chang-Ill Ban, Pohang-si (KR); Hun-Ho Jo, Busan (KR); Ji-Young Kim, Seoul (KR); Eun-Hye Oh, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 144 days.

(21) Appl. No.: 15/119,384

(22) PCT Filed: Jul. 29, 2016

(86) PCT No.: PCT/KR2016/008337
§ 371 (c)(1),
(2) Date: Aug. 16, 2016

(87) PCT Pub. No.: WO2018/021598
PCT Pub. Date: Feb. 1, 2018

(65) Prior Publication Data
US 2018/0169251 A1   Jun. 21, 2018

(30) Foreign Application Priority Data
Jul. 28, 2016   (KR) .................. 10-2016-0096227

(51) Int. Cl.
*C12N 15/11* (2006.01)
*A61K 47/54* (2017.01)
*A61K 31/5365* (2006.01)
*C12N 15/115* (2010.01)
*A61P 31/00* (2006.01)
*C07H 21/04* (2006.01)

(52) U.S. Cl.
CPC ........ *A61K 47/549* (2017.08); *A61K 31/5365* (2013.01); *A61P 31/00* (2018.01); *C07H 21/04* (2013.01); *C12N 15/115* (2013.01)

(58) Field of Classification Search
None
See application file for complete search history.

(56) References Cited

FOREIGN PATENT DOCUMENTS

| CN | 104711263 A | * | 6/2015 |
| KR | 10-2015-0140417 A | | 12/2015 |
| KR | 10-2016-0032989 A | | 3/2016 |

OTHER PUBLICATIONS

CN 104711263 by Chen et al, published in Jun. 2015, with English abstract attached, 10 pages.*
Machine translation of CN 104711263, Sequence of aptamer used for targeting human nasopharyngeal carcinoma cell and application thereof, 2015, pp. 1-5 (Year: 2015).*

* cited by examiner

*Primary Examiner* — Ekaterina Poliakova-Georgantas
(74) *Attorney, Agent, or Firm* — Rabin & Berdo, P.C.

(57) ABSTRACT

This invention relates to a complex for cancer cell chemotherapy and, more particularly, to an AGTR1 aptamer-anticancer drug complex for chemotherapy of cancer cells, which includes a nucleic acid aptamer specifically binding to AGTR1 and an anticancer drug linked with the nucleic acid aptamer, so that AGTR1-positive (overexpressed) breast cancer cells are selectively targeted and killed.

10 Claims, 9 Drawing Sheets
(3 of 9 Drawing Sheet(s) Filed in Color)
Specification includes a Sequence Listing.

AGTR1 APTAMER-ANTICANCER DRUG COMPLEX FOR CANCER CELL CHEMOTHERAPY

CROSS-REFERENCE TO RELATED APPLICATIONS

This application claims the benefit under 35 U.S.C. section 371, of PCT International Application No. PCT/KR/KR2016/008337, filed on Jul. 29, 2016, which claims foreign priority to Korean Patent Application No. KR10-2016-0096227, filed on Jul. 28, 2016, in the Korean Intellectual Property Office, both of which are hereby incorporated by reference in their entireties.

STATEMENT REGARDING SPONSORED RESEARCH OR DEVELOPMENT

This invention was made with Korean Government support of Grant No. HI12C1852, awarded by the Korea Health Industry Development Institute, funded by the Ministry of Health & Welfare, Republic of Korea.

TECHNICAL FIELD

The present invention relates to a complex for cancer cell chemotherapy and, more particularly, to an AGTR1 aptamer-anticancer drug complex for chemotherapy of cancer cells, which includes a nucleic acid aptamer specifically binding to AGTR1 and an anticancer drug linked with the nucleic acid aptamer, so that AGTR1-positive (overexpressed) breast cancer cells are selectively targeted and killed.

BACKGROUND ART

Breast cancer is cancer that frequently occurs in women, and many techniques for the accurate diagnosis and treatment of breast cancer are being developed. Typical methods for the treatment of cancer such as breast cancer and the like include surgery, radiation therapy, and chemotherapy. Among them, chemotherapy is useful in the treatment of cancer by disrupting the replication or metabolism of cancer cells, but is disadvantageous in that it kills not only cancer cells but also normal cells. In order to solve this problem, widely useful is a targeted therapy for the treatment of cancer by targeting a specific protein (e.g. HER2 (Human epidermal growth factor receptor 2), which is overexpressed in breast cancer, or the like) that is expressed in the cancer, as disclosed below.

PATENT LITERATURE

Korean Patent Application Publication No. 10-2015-0140417 (Laid-open date: Dec. 15, 2015), entitled "HER2 Antibody Composition"

Although existing breast cancer-targeted therapy plays a role in treating cancer by targeting HER2, HER2 is overexpressed in only 15 to 20% of all breast cancer patients, and thus, the patients who respond favorably to the existing breast cancer-targeted therapy are limited. Furthermore, the existing breast cancer-targeted therapy using antibodies is problematic because of low stability and high production costs.

DISCLOSURE

Technical Problem

Accordingly, the present invention has been made keeping in mind the above problems encountered in the related art, and the present invention is intended to provide an AGTR1 aptamer-anticancer drug complex for cancer cell chemotherapy, which is able to effectively kill AGTR1-positive breast cancer cells.

In addition, the present invention is intended to provide an AGTR1 aptamer-anticancer drug complex for cancer cell chemotherapy, in which an anticancer drug may be effectively delivered to AGTR1-positive breast cancer cells by targeting AGTR1 using an aptamer.

In addition, the present invention is intended to provide an AGTR1 aptamer-anticancer drug complex for cancer cell chemotherapy, which is formed via disulfide bonding between an aptamer and an anticancer drug, whereby the complex absorbed into cancer cells is split by glutathione present in the cytosol, and thus the release of the drug to non-target regions may be inhibited.

Technical Solution

The present invention is accomplished by exemplary embodiments as follows.

An embodiment of the present invention provides a complex for cancer cell chemotherapy, comprising a nucleic acid aptamer specifically binding to AGTR1 and an anticancer drug linked with the nucleic acid aptamer.

Also, the complex for cancer cell chemotherapy according to the present invention may be foiled via disulfide bonding between the nucleic acid aptamer and the anticancer drug.

Also, in the complex for cancer cell chemotherapy according to the present invention, a thiol group may be introduced to a 3' terminus of the nucleic acid aptamer, and the anticancer drug may be an anticancer drug having a thiol group, and thus the disulfide bonding may be formed between the nucleic acid aptamer and the anticancer drug.

Also, in the complex for cancer cell chemotherapy according to the present invention, the nucleic acid aptamer may have any one base sequence of SEQ ID NOS:1 to 6.

Also, in the complex for cancer cell chemotherapy according to the present invention, the nucleic acid aptamer may have a base sequence of SEQ ID NO:4.

Also, in the complex for cancer cell chemotherapy according to the present invention, the anticancer drug may include DM1.

Also, the complex for cancer cell chemotherapy according to the present invention may be used for the treatment of breast cancer.

Also, the complex for cancer cell chemotherapy according to the present invention may be absorbed into AGTR1-positive breast cancer cells, so that the disulfide bonding is broken by glutathione present in the cytosol to thus isolate the anticancer drug.

Another embodiment of the present invention provides a method of manufacturing a complex for cancer cell chemotherapy, comprising an aptamer preparation step of preparing a nucleic acid aptamer having an aptamer base sequence specifically binding to AGTR1, and a complex formation step of forming an aptamer-anticancer drug complex by reacting the aptamer prepared in the aptamer preparation step with an anticancer drug.

Also, in the method according to the present invention, the aptamer preparation step may include forming a nucleic acid aptamer having any one base sequence of SEQ ID NOS:1 to 6 specifically binding to AGTR1, introducing a thiol group to a 3' terminus of the nucleic acid aptamer, and activating a 3' thiol group by reaction with dithiothreitol in a triethylammonium acetate buffer.

Also, in the method according to the present invention, the complex formation step may include providing DM1 dissolved in dimethyl sulfoxide, and reacting the aptamer and the DM1 at a ratio of 1:1000 in a potassium phosphate buffer containing dimethyl sulfoxide (DMSO) and ethylenediaminetetraacetic acid (EDTA), thus forming the aptamer-anticancer drug complex.

Still another embodiment of the present invention provides a nucleic acid aptamer specifically binding to AGTR1, having any one base sequence of SEQ ID NOS:1 to 6.

Yet another embodiment of the present invention provides a nucleic acid aptamer specifically binding to AGTR1, having a base sequence of SEQ ID NO:4.

Advantageous Effects

According to exemplary embodiments of the present invention, the following effects may be obtained.

The present invention is effective at killing AGTR1-positive breast cancer cells.

Also, the present invention is effective at delivering an anticancer drug to AGTR1-positive breast cancer cells by targeting AGTR1 using an aptamer.

Also, according to the present invention, when the complex, which is foiled via disulfide bonding between the aptamer and the anticancer drug, is absorbed into cancer cells, it is split by means of glutathione present in the cytosol, thus effectively inhibiting the release of a drug to non-target regions.

DESCRIPTION OF DRAWINGS

The patent or application file contains at least one drawing executed in color. Copies of this patent or patent application publication with color drawing(s) will be provided by the Office upon request and payment of the necessary fee.

MODE FOR INVENTION

Hereinafter, a detailed description will be given of an AGTR1 aptamer-anticancer drug complex for cancer cell chemotherapy according to the present invention, with reference to the appended drawings. Unless otherwise defined, all terms used herein have the same meaning as commonly understood by one of ordinary skill in the art to which the present invention belongs. If the meaning of the term used herein conflicts with the general meaning thereof, it accords to the definition used herein. In the following description of the present invention, detailed descriptions of known constructions and functions incorporated herein will be omitted when they may make the gist of the present invention unclear. As used herein, when any part "includes" any element, it means that other elements are not precluded but may be further included, unless otherwise mentioned.

According to an embodiment of the present invention, a complex for cancer cell chemotherapy includes a nucleic acid aptamer specifically binding to AGTR1 and an anticancer drug linked with the nucleic acid aptamer. AGTR1 (Angiotensin II type I receptor) is a receptor that binds to angiotensin II to thus trigger an intracellular mechanism, and is overexpressed in 20% of breast cancer patients. In the following examples, the proliferation of breast cancer was confirmed by observing overexpression of AGTR1 in the MCF7 breast cancer cell line. Therefore, according to the present invention, an anticancer drug may be effectively delivered to AGTR1-positive breast cancer cells by targeting AGTR1 using an aptamer, thereby effectively treating AGTR1-overexpressed breast cancer.

As used herein, the term "nucleic acid aptamer" refers to single-stranded DNA or RNA having high affinity and selectivity to a specific target material. The aptamer advantageously exhibits higher affinity to a target material than an antibody, exhibits high thermal stability to thus enable long-term storage at room temperature, facilitates chemical modification to thus be relatively simply produced at low cost, and may be regenerated within a short time even when degenerated. Hence, in the present invention, is a nucleic acid aptamer specifically binding to AGTR1 upon the formation of the complex is adopted. The nucleic acid aptamer may have various aptamer base sequences specifically binding to AGTR1, but preferably has any one base sequence of SEQ ID NOS:1 to 6, and more preferably the base sequence of SEQ ID NO:4. The process of selecting the nucleic acid aptamer having any one base sequence of SEQ ID NOS:1 to 6 specifically binding to AGTR1 is described later. In order to form a complex thereof with the anticancer drug, a thiol group is introduced to the 3' terminus of the nucleic acid aptamer.

As the anticancer drug, any drug may be used so long as it is linked with the nucleic acid aptamer to thus kill cancer cells. Preferably useful is a drug having a thiol group, and more preferably useful is maytansine (a maytansinoid, DM1). Maytansine (DM1) is a drug which is linked to a tubulin protein for forming mitotic spindles in the G2/M phase of a cell cycle so that the function of tubulin is inhibited to thus induce the formation of abnormal mitotic spindles, thus suppressing the normal arrangement of chromosomes, thereby preventing mitosis and leading to the apoptosis of cancer cells. The 3' terminus of the nucleic acid aptamer is introduced with a thiol group, and as the anticancer drug, an anticancer drug having a thiol group is used, whereby the nucleic acid aptamer and the anticancer drug are linked via disulfide bonding, thus forming a complex. Since AGTR1, which is overexpressed, is found in breast cancer, the complex includes the nucleic acid aptamer for targeting AGTR1 to thereby effectively target the breast cancer cells. As for the complex that is formed via disulfide bonding, glutathione, which breaks disulfide bonds, is present in the cytosol but absent from the blood and lymph, and thus the complex of the present invention is absorbed into breast cancer cells and then the anticancer drug is isolated, thereby effectively releasing the drug to cancer cells, rather than non-target regions, ultimately decreasing side effects and increasing the effect of cancer cell apoptosis.

Another embodiment of the present invention addresses a method of manufacturing a complex for cancer cell chemotherapy, including an aptamer preparation step of preparing a nucleic acid aptamer having an aptamer base sequence specifically binding to AGTR1, and a complex formation step of forming an aptamer-anticancer drug complex by reacting the aptamer prepared in the aptamer preparation step with an anticancer drug.

In the aptamer preparation step, a nucleic acid aptamer having an aptamer base sequence specifically binding to AGTR1 is prepared. Particularly, a nucleic acid aptamer having any one base sequence of SEQ ID NOS:1 to 6, specifically binding to AGTR1, is formed, and a thiol group is introduced to the 3' terminus of the nucleic acid aptamer (to substitute OH with SH), after which the reaction with dithiothreitol in a triethylammonium acetate buffer is carried out, thereby activating the 3' thiol group, yielding the nucleic acid aptamer.

In the complex formation step, the aptamer prepared in the aptamer preparation step is reacted with the anticancer drug, thus forming the aptamer-anticancer drug complex. Particularly, DM1 dissolved in dimethyl sulfoxide is provided, and the aptamer and DM1 are reacted at a ratio of 1:1000 in a potassium phosphate buffer containing DMSO and EDTA, thereby obtaining the aptamer-anticancer drug complex.

Still another embodiment of the present invention addresses a pharmaceutical composition for the treatment of breast cancer, including the above complex for cancer cell chemotherapy.

The pharmaceutical composition for the treatment of breast cancer may include (a) a pharmaceutically effective amount of the above complex for cancer cell chemotherapy; and (b) a pharmaceutically acceptable carrier.

As used herein, the term "pharmaceutically effective amount" may refer to an amount sufficient to achieve the effect of breast cancer therapy.

In the pharmaceutical composition for the treatment of breast cancer, the pharmaceutically acceptable carrier may include those typically used for formulations, and examples thereof may include, but are not limited to, lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methyl cellulose, methylhydroxybenzoate, propylhydroxybenzoate, talc, magnesium stearate, and mineral oil. The pharmaceutical composition for the treatment of breast cancer may further include, in addition to the above components, a lubricant, a humectant, a sweetener, a flavoring agent, an emulsifier, a suspending agent, a preservative, etc.

The pharmaceutical composition for the treatment of breast cancer may be administered orally or parenterally (e.g. intravenous, intraperitoneal, intramuscular, subcutaneous, or topical administration).

The appropriate dose of the pharmaceutical composition for the treatment of breast cancer may vary depending on the formulation method, administration mode, the subject's age, body weight, and gender, disease severity, diet, administration time, administration route, excretion rate, and response sensitivity, and doctors who are normally trained may easily determine and prescribe a dose that is effective for desired treatment.

According to a method that may be easily executed by those skilled in the art to which the present invention belongs, the pharmaceutical composition for the treatment of breast cancer may be formulated together with a pharmaceutically acceptable carrier and/or excipient into a unit dose form, or may be packed in multiple-dose containers. As such, the formulation may be provided in the form of a solution, suspension or emulsion in oil or an aqueous medium, or in the form of an extract, a powder, a granule, a tablet, or a capsule, or may further include a dispersant or a stabilizer.

A better understanding of the present invention may be obtained through the following examples which are set forth to illustrate, but are not to be construed to limit the scope of the present invention.

<Example 1> Formation of AGTR1-Overexpressed Cell Line and Evaluation of Properties Thereof (1) Each of human breast cancer cell lines, including SK-BR-3, MCF7, and BT474, was cultured under conditions of 5% $CO_2$ and 37° C. in Dulbecco's modified Eagle's medium (DMEM) containing 10% fetal bovine serum (FBS), streptomycin-penicillin (100 U/ml) and Fungizone (0.625 μg/ml).

(2) AGTR1-overexpressed cells were produced using a lentiviral system, and AGTR1 genes were amplified by PCR using a specific primer (enzyme site: NheI/NotI) and inserted into a dual promoter lentivector (CD550A-1, System Biosciences, USA). Viruses were produced with lentiviral packaging and then transduced into HEK293T producer cells. Pseudoviral particles were collected via centrifugation, concentrated, and then transduced into the cultured SK-BR-3, MCF7, and BT474 cells. After the transfection, puromycin selection (final concentration of puromycin: 3 μg/ml) was performed, and single colonies were isolated from the vessel, thus obtaining individual AGTR1-overexpressed SK-BR-3, MCF7, and BT474 cell lines. The AGTR1-overexpressed (positive) breast cancer SK-BR-3, MCF7, and BT474 cell lines were used for the following testing.

Figure 1:
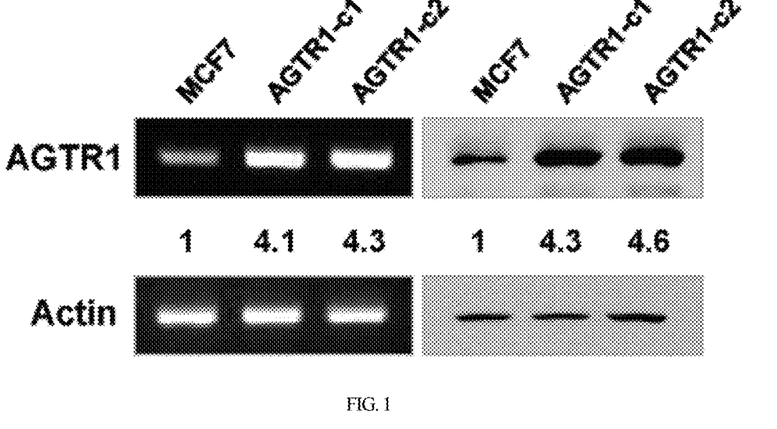
FIG. 1 shows images depicting the extent of expression of AGTR1 in breast cancer cell lines produced so as to overexpress AGTR1.

(3) The mRNA and protein levels of parental MCF7 and AGTR1-overexpressed MCF7 (AGTR1 clone number 1 (AGTR1-c1), and AGTR1 clone number 2 (AGTR1-c2)) obtained in (2) of Example 1 were measured via RT-PCR and Western blot, and the expression of AGTR1 was quantified and numbered. The results are shown in FIG. 1.

In the RT-PCR, total RNA was extracted using an RNeasy mini kit (Qiagen, Valencia, Calif., USA), and the amplification of transcription was conducted by means of a reverse transcriptase-polymerase chain reaction (RT-PCR) using 1 μg/μl RNA, Molony Murine Leukemia Virus reverse transcriptase (MMLV; Gibco/BRL, Gaithersburg, Md., USA) and oligo-d(T)15 primers (Roche Applied Sciences). PCR amplification was implemented via Takara PCR Thelival Cycler (Thermo Scientific Inc., Rockford, Ill.). The PCR products were separated on 1.2% agarose gels, and visualized using a Gel Doc™ XR+System (Bio-Rad Laboratories).

In the Western blot, the above cells were lysed in a lysis buffer (30 mM NaCl, 0.5% Triton X-100, 50 mM Tris-HCl; pH 7.4) containing phosphatase and a protease inhibitor, and the supernatant was collected and then the protein was concentrated using a Bradford protein assay kit. 30 μg of the protein was subjected to SDS-PAGE and electrophoresed with a nitrocellulose membrane. The membrane was cultured overnight at 4° C. with primary antibodies diluted in 5% bovine serum albumin (BSA) and then cultured with horseradish peroxidase (HRP)-conjugated rabbit IgG (1:3000-1:10,000). Signal intensity was measured using an Enhanced Chemiluminescence Kit and an X-ray film, and quantified with AlphaEaseFC software.

Figure 2:
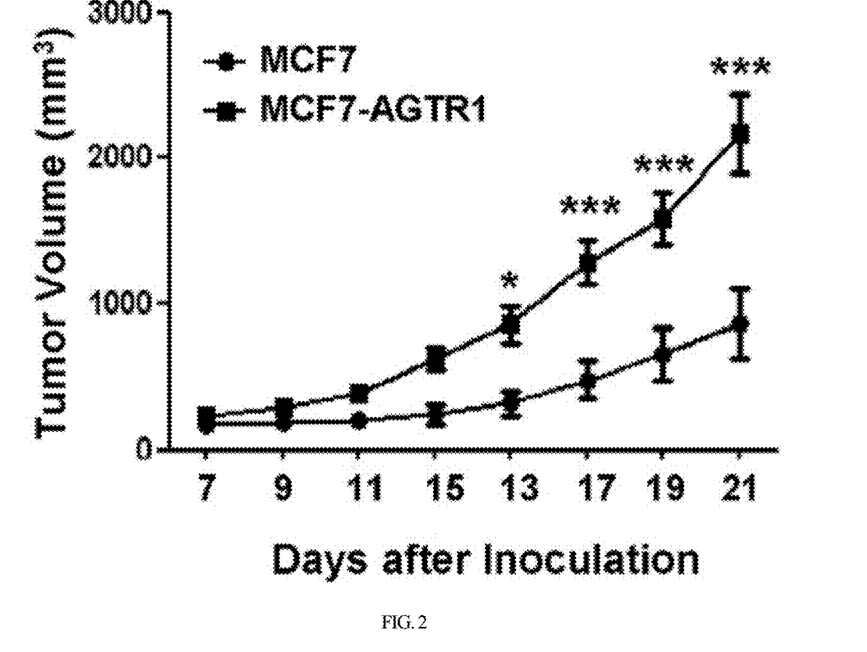
FIG. 2 shows the results of measurement of the tumor volume in an animal to which the AGTR1-positive breast cancer cell line is inoculated.

(4) AGTR1-overexpressed MCF7 (MCF7-AGTR1) cancer cells ($3 \times 10^6$ cells) and MCF7 cancer cells ($3 \times 10^6$ cells) were inoculated into the fourth mammary fat pads of immunodeficient 6-week-old female BALB/c nude mice to generate tumors, after which the tumor volume was measured for 21 days. The results are shown in FIG. 2. The tumor volume (V) was measured using a caliper and calculated according to V=(length×width$^2$)/2.

(5) As shown in FIG. 1, compared to parental-MCF7, the appearance of AGTR1-overexpressed MCF7 (AGTR1-c1, AGTR1-c2) indicated that the amount of expressed AGTR1 was increased at least 4 times, from which AGTR1-overexpressed cell lines can be confirmed to effectively result. As shown in FIG. 2, the volume of tumors to which AGTR1-overexpressed breast cancer cells were inoculated was notably large, and there was a significant difference in the tumor size between the two groups after 2 weeks. Thereby, AGTR1 can be confirmed to serve as a novel biomarker of breast cancer.

<Example 2> Selection of Aptamer Specifically Binding to AGTR1

(1) Synthesis of Nucleic Acid Library

A nucleic acid library (ssDNA library), which has fixed sequence regions for PCR at both termini thereof and a random sequence of 40 bases at the center thereof, was synthesized. The ssDNA library was represented by 5'-ATC-CAGAGTGACGCAGCA (SEQ ID NO:7)-N40-TGGA-CACGGTGGCTTAGT (SEQ ID NO:8)-3', and both termini thereof were composed of fixed base sequence regions annealed with primer pairs, and the center thereof had a randomly arranged base sequence region (N40). Here, N40 indicates a random sequence of 40 bases comprising A, T, G, and C.

(2) Culture of Cells and Preparation of Nucleic Acid Library

1) As produced in Example 1, the AGTR1-positive cell line (AGTR1-overexpressed SK-BR-3) and the AGTR1-negative cell line (SK-BR-3) were cultured to a confluency of 90% or more and then washed two times with a washing buffer (DPBS (+Ca$^{2+}$, +Mg$^{2+}$), 6.25 mM glucose, 5 mM MgCl$_2$).

2) The synthesized ssDNA library was adjusted to a final concentration of 1 μM with 1 ml of a binding buffer (DPBS (+Ca$^{2+}$, +Mg$^{2+}$), 6.25 mM glucose, 5 mM MgCl$_2$, 0.1% (w/v) BSA, 0.01% (w/v) tRNA), boiled for 5 min, and then stored in an ice water bath for 1 hr.

(3) Selection of ssDNA

1) The cooled DNA library was treated with the AGTR1-positive cell line and allowed to react at 4° C. for 1 hr, the buffer was removed using an aspirator, washing was performed two times using 2 ml of a washing buffer, and the cells attached to the surface of the plate were collected into a binding buffer using a scraper, after which, in order to remove DNA from the cells, boiling was conducted for 10 min, followed by centrifugation at 13000 rpm for 10 min.

2) Only the supernatant was reacted at 4° C. for 1 hr in the AGTR1-negative cell line, and the unbound sequences were collected and DNA sequences were amplified via PCR.

3) The above procedures were regarded as a single round, and the finally amplified sequences were prepared for the library of the next round, and 15 rounds were conducted.

(4) Analysis of ssDNA Base Sequence 1) ssDNA finally obtained in (3) of Example 2 was cloned using a TOPO TA cloning kit, and the sequences thereof were analyzed.

2) As results, ssDNA having 6 different sequences was ensured. The 6 different ssDNA base sequences, having high affinity to AGTR1 and specifically binding thereto, are shown in Table 1 below.

TABLE 1

| SEQ ID NO: | Base sequence (Sequence of random region) |
|---|---|
| 1 | TCTCCATGCTTTATAACGTGTATGAGGGAAGTTTGTTGTT |
| 2 | TCTGAGAATAGTGGTTTGCTGTATGGTGGGCGTTGAAAGAGGGG |
| 3 | TGGTGTGGTTGGTAAGGATTTGGTGCGTTCTTGCTTCGACTTCCGTCATCA |
| 4 | AAGTCGTCTTTGCCAAATACCGGTCTGTCGGTGGGTATTG |
| 5 | CGCCTCGAAGTACCGGTATGTCGGTGGGTAGTTCGGTGTA |
| 6 | CCCACGGTGCATTCTATCATAGTGCTTTCATTTAGTCCGA |

Figure 3:
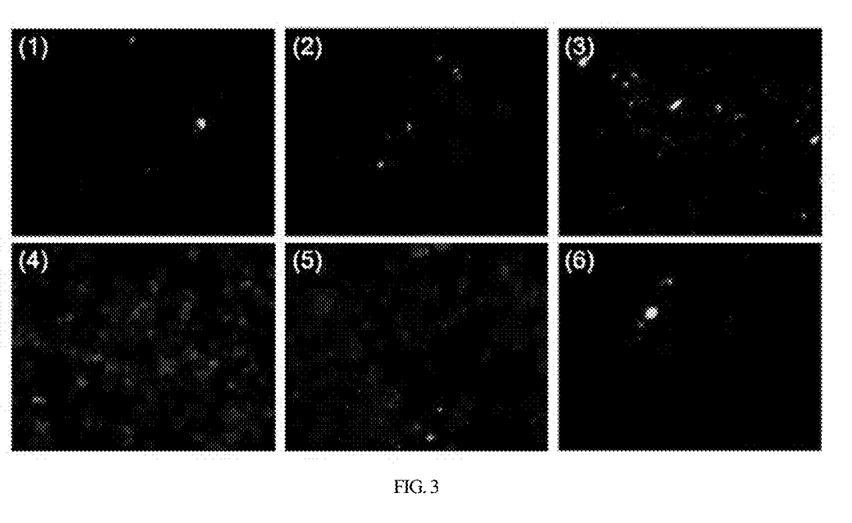
FIG. 3 shows confocal microscopy images depicting the ability of aptamer base sequences to bind to AGTR1-positive breast cancer cells.

(5) Selection of Aptamer for Use in Aptamer-Anticancer Drug Complex 1) 100 μl ($10^7$ cells) of target cells, namely AGTR1-overexpressed SK-BR-3, and 100 μl of 500 nM aptamer were reacted at room temperature and imaged using a confocal microscope. The results are shown in FIG. 3. The aptamers have respective base sequences of SEQ ID NOS:1 to 6, the end of each of which is coupled with a fluorescence dye Cy3.

2) As shown in FIG. 3, in the fourth image (4) resulting from reaction of the aptamer having the base sequence of SEQ ID NO:4, internalization can be confirmed to occur at the strongest fluorescence intensity. Hence, the aptamer having the base sequence of SEQ ID NO:4, which has the greatest bindability to AGTR1-positive breast cancer cells, was chosen as an aptamer for use in the aptamer-anticancer drug complex.

<Example 3> Formation of Aptamer (1) A nucleic acid (DNA) aptamer [5'-AAGTCGTCTTT-GCCAAATACCGGTCTGTCGGTGGGTATTG-3' (SEQ ID NO:4)] having an aptamer base sequence specifically binding to AGTR1 was designed, and a thiol group was introduced to the 3' terminus of the nucleic acid aptamer (to substitute OH with SH).

(2) Thereafter, the nucleic acid aptamer was reacted at room temperature for 15 min with 10 μl of 1.0 M dithiothreitol (DTT) in a 0.1 M triethylammonium acetate (TEAA) buffer, whereby the 3' thiol group was activated, and extraction was additionally performed three or more times using ethyl acetate to remove excess DTT.

<Example 4> Formation of Aptamer-Anticancer Drug Complex (Aptamer-DM1)

The aptamer finally obtained in Example 3 was reacted with an anticancer drug (DM1), thereby manufacturing an aptamer-anticancer drug complex. Particularly, DM1 was dissolved in dimethyl sulfoxide (DMSO) to yield a 10 mM stock, and the aptamer-DM1 complex was formed in a 100 mM potassium phosphate buffer (pH 7.0) containing 50% DMSO and 2 mM ethylenediaminetetraacetic acid (EDTA). As such, the aptamer and DM1 were reacted at a ratio of 1:1000 at room temperature for 48 hr.

<Example 5> Purification of Aptamer and Aptamer-Anticancer Drug Complex

The aptamer finally obtained in Example 3 and the aptamer-anticancer drug complex finally obtained in Example 4 were purified through high-performance liquid chromatography (HPLC). Separation was performed using an Eclipse XDB-C18 column through the gradient of a binding buffer (95% 0.1 M TEAA, 5% acetonitrile) and an elution buffer (50% 0.1 M TEAA, 50% acetonitrile). The peaks of HPLC were analyzed using mass spectroscopy, among which only the peaks that matched the molecular weights of the aptamer and the aptamer-anticancer drug complex were selected. The aptamer (Aptamer) and the aptamer-anticancer drug complex (Aptamer-DM1), purified in Example 5, were used for the following testing.

Figure 4:
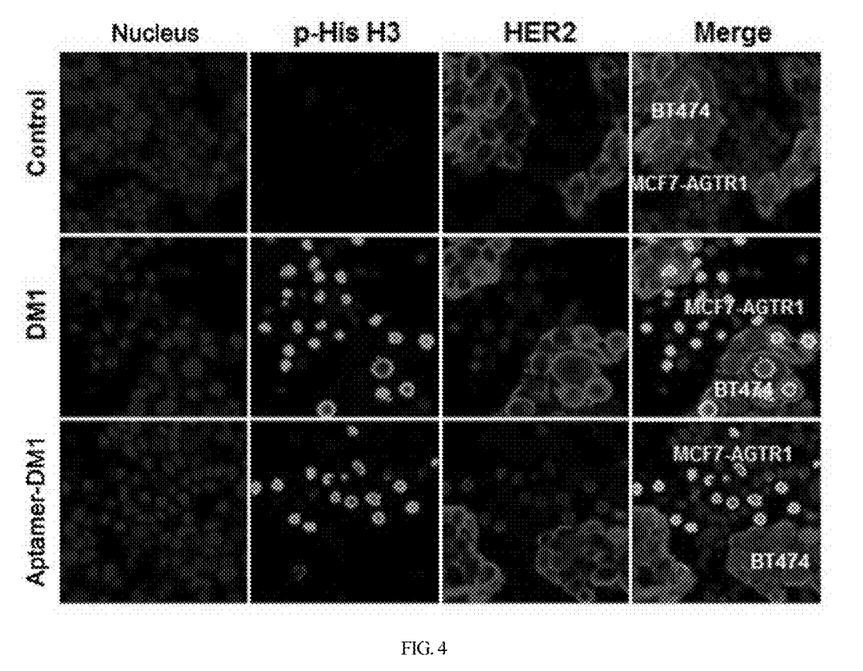
FIG. 4 shows confocal microscopy images depicting the targeting capability of the complex in the AGTR1-positive breast cancer cell line and the AGTR1-negative breast cancer cell line, which are co-cultured.
Figure 5:
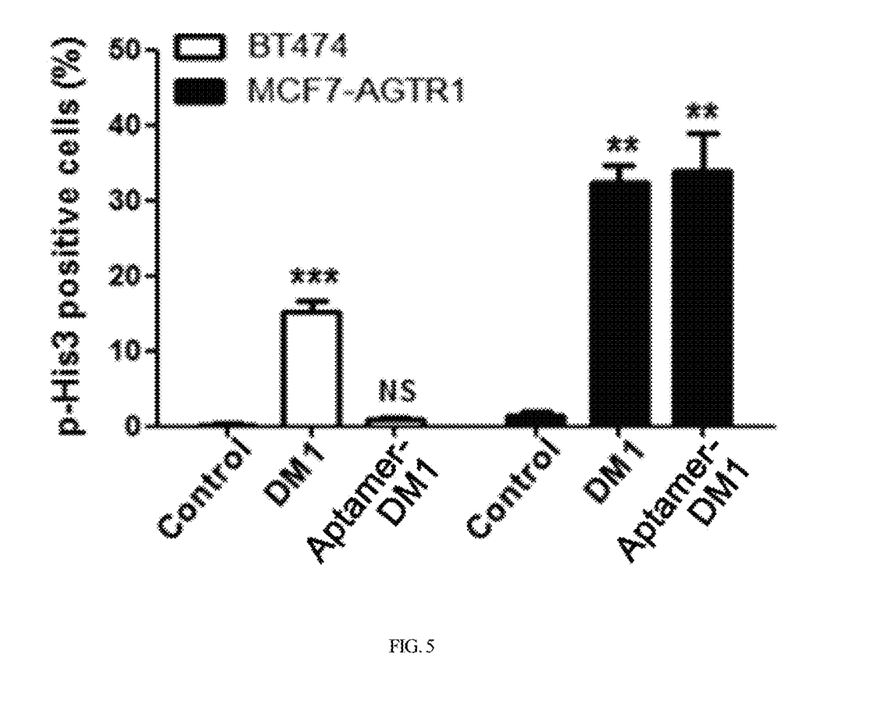
FIG. 5 shows the results of quantification of the number of cells in which His3 is detected depending on whether AGTR1 is expressed or not.

<Example 6> Evaluation of Targeting Capability of Aptamer-Anticancer Drug Complex to AGTR1-Overexpressed Breast Cancer Cells (1) As produced in Example 1, the AGTR1-positive breast cancer MCF7 cell line (MCF7-AGTR1) and the AGTR1-negative breast cancer BT474 cell line (typically, MCF7 is a HER2-negative breast cancer cell line and BT474 is a HER2-positive breast cancer cell line) were co-cultured at a ratio of 1:1, and HER2 and a mitotic arrest marker, namely phospho-Histone H3 (p-His3), were stained with ICC, and the nuclei of which were stained with DAPI, and were then treated with a control (DMSO), DM1, and Aptamer-DM1 at a concentration of 10 nM for 24 hr. Thereafter, the nuclei (blue), p-His3 (green), and HER2 (red) were imaged using a confocal microscope. The results are shown in FIG. 4. The number of cells in which p-His3 was detected was quantified based on whether or not AGTR1 was expressed. The results are shown in FIG. 5.

During the staining procedure, the MCF7-AGTR1 and BT474 cells cultured on 8-well chamber slides were fixed with 4% paraformaldehyde, washed with PBS, and cultured for 10 min with 0.2% Triton X-100. Thereafter, the cells were cultured overnight at 4° C. with primary antibodies in an antibody dilution buffer and then cultured at room temperature for 2 hr with fluorescence-conjugated secondary antibodies. Thereafter, the cells were mounted on ProLong Gold Antifade Reagent containing DAPI (4',6'-diamidine-2'-phenylindole dihydrochloride).

(2) As shown in FIG. 4, in the control group, the cells in which HER2 was expressed are deemed to be BT474 and the cells in which HER2 was not expressed are deemed to be MCF7-AGTR1. In the DM1-treated group, the expression of p-His3 was observed regardless of whether HER2 was expressed or not, but in the group treated with Aptamer-DM1, p-His3 was detected only in the MCF7-AGTR1 cells in which HER2 was not expressed. As shown in FIG. 5, in the group treated with Aptamer-DM1, the proportion of cells in which p-His3 was detected was high in the AGTR1-positive cell line but low in the AGTR1-negative cell line. This is because Aptamer-DM1 was introduced into the cytosol of the AGTR1-expressed cell line, and thus mitotic arrest was induced by the isolated DM1, and simultaneously, the expression of p-His3 was increased, from which Aptamer-DM1 can be confirmed to specifically target only AGTR1.

<Example 7> Evaluation of Ability of Aptamer-Anticancer Drug Complex to Selectively Kill AGTR1-Overexpressed Breast Cancer Cells (1) The AGTR1-positive breast cancer cell line (MCF7-AGTR1) and the AGTR1-negative breast cancer cell line (BT474) were treated with a control (DMSO), DM1, Aptamer, and Aptamer-DM1 at a concentration of 10 nM for 48 hr, after which the cells were acquired and fixed with 95% ethanol containing 0.5% Tween-20 for 24 hr and cultured for 30 min with propidium iodide (PI, 50 μg/ml) and RNase (50 μg/ml). Thereafter, the apoptosis rate (sub-G1%) of cancer cells was measured through DNA content analysis using flow cytometry. The results are shown in FIG. 6.

(2) Typically, the cell cycle includes, depending on the amount of DNA in cells, G1 (cell growth phase), S (cell replication phase), and G2/M (cell mitotic phase). The induction of apoptosis is accompanied by DNA fragmentation, and thus DNA replication and division become impossible, and the amount of DNA is remarkably decreased compared to the G1 phase. The results of apoptosis are represented by the percentage of sub-G1 in the cell cycle.

Figure 6:
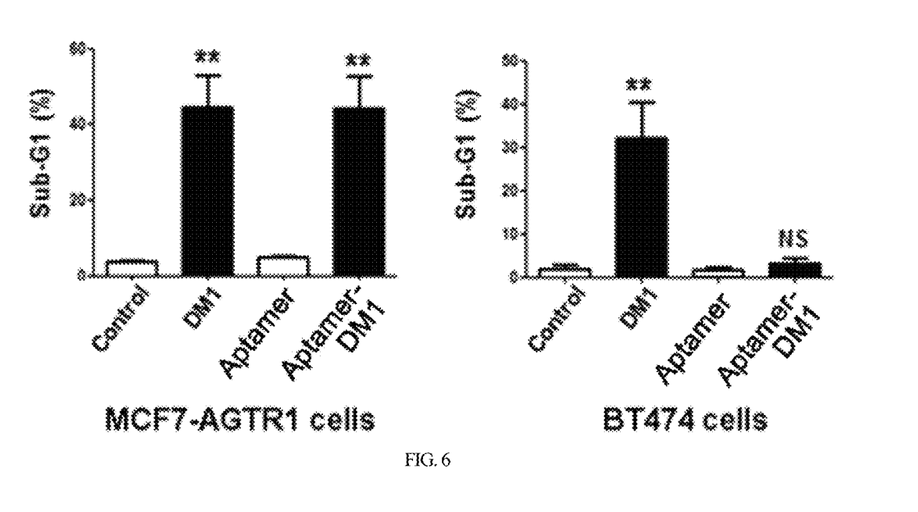
FIG. 6 shows the ability of the complex to selectively kill AGTR1-positive breast cancer cells.

(3) As shown in FIG. 6, the control group and the group treated with Aptamer had remarkably low apoptosis rates in all cell lines, but in the DM1-treated group, relatively high apoptosis was induced in all cell lines. In the group treated with Aptamer-DM1, the apoptosis rate was high in the AGTR1-positive cell line but low in the AGTR1-negative cell line. Thereby, Aptamer-DM1 can be confirmed to specifically induce apoptosis only in the positive breast cancer cell line in which AGTR1 is expressed.

Figure 7:
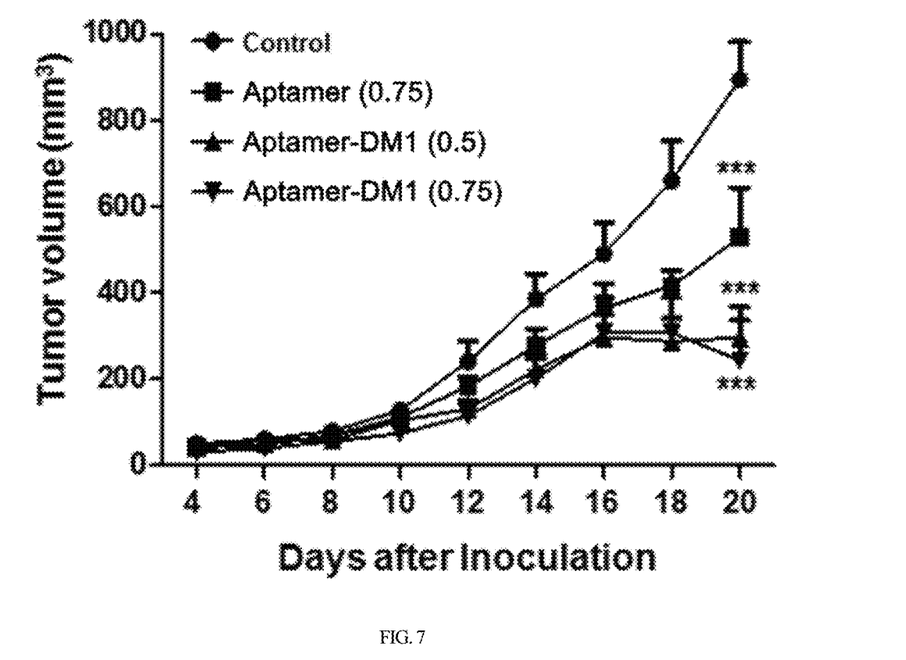
FIG. 7 shows the results of measurement of the tumor volume to evaluate the ability of the complex to selectively kill AGTR1-positive breast cancer cells in breast cancer disease animal models.
Figure 8:
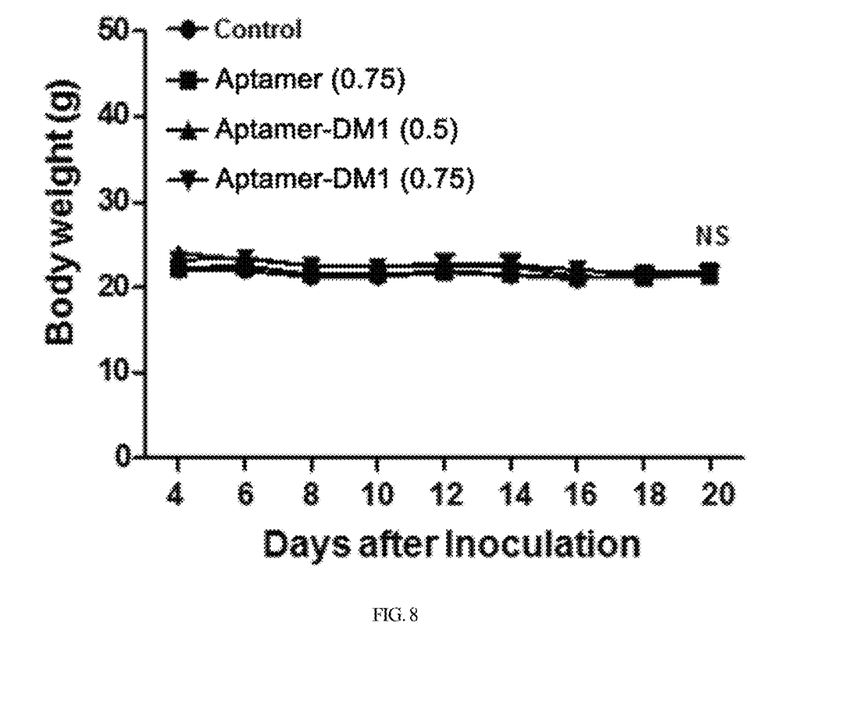
FIG. 8 shows the results of measurement of the body weight of animals to evaluate the ability of the complex to selectively kill AGTR1-positive breast cancer cells in breast cancer disease animal models.
Figure 9:
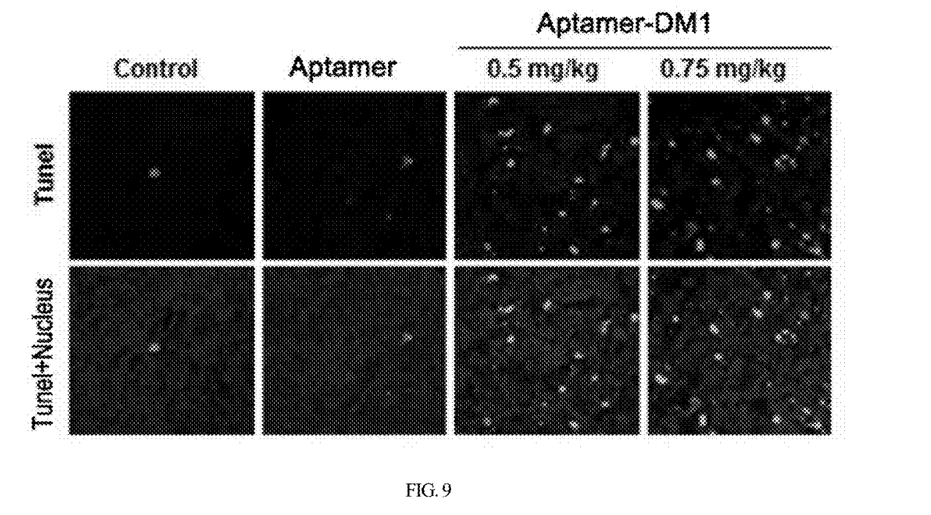
FIG. 9 shows images depicting the results of a TUNEL assay to evaluate the ability of the complex to selectively kill AGTR1-positive breast cancer cells in breast cancer disease animal models.

<Example 8> Evaluation of Anticancer Effect Of Aptamer-Anticancer Drug Complex in Breast Cancer Disease Animal Model (1) Starting from the 4th day after MCF7-AGTR1 cancer cells ($3\times10^6$ cells) were inoculated into the fourth mammary fat pads of immunodeficient 6-week-old female BALB/c nude mice, Aptamer (0.75 mg/kg) and Aptamer-DM1 (0.5 mg/kg, 0.75 mg/kg) were intraperitoneally administered three times a week. Then, the tumor volume was measured for 3 weeks. The results are shown in FIG. 7. The body weights of mice were measured for 3 weeks. The results thereof are shown in FIG. 8, and the results of a TUNEL assay are shown in FIG. 9. The tumor volume (V) was measured using a caliper and calculated according to $V=(length\times width^2)/2$. In a Terminal deoxynucleotidyl transferase dUTP Nick End Labeling (TUNEL) assay, the tumors were removed from the mice, fixed in 10% neutral buffered formalin, and embedded in paraffin. The 4 μm thick tissue section was mounted on a positively charged glass slide, deparaffinized with xylene, and dehydrated through a graded alcohol series. After antigen retrieval, the above tissue section was boiled in a citric acid buffer (pH 6.0) and immunofluorescence was performed. In situ TUNEL was performed on the above tissue section using a TUNEL kit (Roche Applied Sciences, Penzberg, GER), and the images thereof were obtained using a confocal scanning microscope.

(2) As shown in FIG. 7, in all the groups administered with Aptamer-DM1 at 0.5 mg/kg and 0.75 mg/kg, the growth of tumors was significantly decreased, and moreover, the growth of tumors was partially inhibited even in the group treated with Aptamer. As shown in FIG. 8, no changes in body weight based on the administration of the drug were observed in all the test groups, compared to the control group. As shown in FIG. 9, based on the results of apoptosis through the TUNEL assay, the group treated with Aptamer-DM1 significantly increased the number of TUNEL-positive cells. Thereby, Aptamer-DM1 can be confirmed to exhibit anticancer effects on AGTR1-overexpressed breast cancer in animal models.

Although the variety of embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A complex for cancer cell chemotherapy, comprising a nucleic acid aptamer specifically binding to AGTR1 and an anticancer drug linked with the nucleic acid aptamer, wherein the nucleic acid aptamer has any one base sequence of SEQ ID NOS: 1, 3 to 6.

2. The complex of claim 1, wherein the complex is formed via disulfide bonding between the nucleic acid aptamer and the anticancer drug.

3. The complex of claim 2, wherein a thiol group is introduced to a 3' terminus of the nucleic acid aptamer, and the anticancer drug is an anticancer drug having a thiol group, and thus the disulfide bonding is formed between the nucleic acid aptamer and the anticancer drug.

4. The complex of claim 1, wherein the nucleic acid aptamer has a base sequence of SEQ ID NO: 4.

5. The complex of claim 2, wherein the anticancer drug comprises DM1.

6. A nucleic acid aptamer specifically binding to AGTR1, having any one base sequence of SEQ ID NOS: 1, 3 to 6.

7. A nucleic acid aptamer specifically binding to AGTR1, having a base sequence of SEQ ID NO: 4.

8. A method of manufacturing a complex for cancer cell chemotherapy, comprising:
   an aptamer preparation step of preparing a nucleic acid aptamer having an aptamer base sequence specifically binding to AGTR1, wherein the nucleic acid aptamer has any one base sequence of SEQ ID NOS: 1, 3 to 6; and
   a complex formation step of forming an aptamer-anticancer drug complex by reacting the aptamer prepared in the aptamer preparation step with an anticancer drug.

9. The method of claim 8, wherein the aptamer preparation step comprises, introducing a thiol group to a 3' terminus of the nucleic acid aptamer, and activating a 3' thiol group by reaction with dithiothreitol in a triethylammonium acetate buffer.

10. The method of claim 8, wherein the complex formation step comprises providing DM1 dissolved in dimethyl sulfoxide, and reacting the aptamer and the DM1 at a ratio of 1:1000 in a potassium phosphate buffer containing dimethyl sulfoxide (DMSO) and ethylenediaminetetraacetic acid (EDTA), thus forming the aptamer-anticancer drug complex.

* * * * *

```
                          SEQUENCE LISTING

<160> NUMBER OF SEQ ID NOS: 8

<210> SEQ ID NO 1
<211> LENGTH: 40
<212> TYPE: DNA
<213> ORGANISM: Artificial Sequence
<220> FEATURE:
<223> OTHER INFORMATION: AGTR1 aptamer

<400> SEQUENCE: 1
tctccatgct ttataacgtg tatgagggaa gtttgttgtt                             40

<210> SEQ ID NO 2
<211> LENGTH: 44
<212> TYPE: DNA
<213> ORGANISM: Artificial Sequence
<220> FEATURE:
<223> OTHER INFORMATION: AGTR1 aptamer

<400> SEQUENCE: 2
tctgagaata gtggtttgct gtatggtggg cgttgaaaga gggg                        44

<210> SEQ ID NO 3
<211> LENGTH: 51
<212> TYPE: DNA
<213> ORGANISM: Artificial Sequence
<220> FEATURE:
<223> OTHER INFORMATION: AGTR1 aptamer

<400> SEQUENCE: 3
tggtgtggtt ggtaaggatt tggtgcgttc ttgcttcgac ttccgtcatc a                51

<210> SEQ ID NO 4
<211> LENGTH: 40
<212> TYPE: DNA
<213> ORGANISM: Artificial Sequence
<220> FEATURE:
<223> OTHER INFORMATION: AGTR1 aptamer

<400> SEQUENCE: 4
aagtcgtctt tgccaaatac cggtctgtcg gtgggtattg                             40

<210> SEQ ID NO 5
<211> LENGTH: 40
<212> TYPE: DNA
<213> ORGANISM: Artificial Sequence
<220> FEATURE:
<223> OTHER INFORMATION: AGTR1 aptamer

<400> SEQUENCE: 5
cgcctcgaag taccggtatg tcggtgggta gttcggtgta                             40
```

```
<210> SEQ ID NO 6
<211> LENGTH: 40
<212> TYPE: DNA
<213> ORGANISM: Artificial Sequence
<220> FEATURE:
<223> OTHER INFORMATION: AGTR1 aptamer

<400> SEQUENCE: 6
cccacggtgc attctatcat agtgctttca tttagtccga                          40

<210> SEQ ID NO 7
<211> LENGTH: 18
<212> TYPE: DNA
<213> ORGANISM: Artificial Sequence
<220> FEATURE:
<223> OTHER INFORMATION: preserved region of ssDNA library

<400> SEQUENCE: 7
atccagagtg acgcagca                                                  18

<210> SEQ ID NO 8
<211> LENGTH: 18
<212> TYPE: DNA
<213> ORGANISM: Artificial Sequence
<220> FEATURE:
<223> OTHER INFORMATION: preserved region of ssDNA library

<400> SEQUENCE: 8
tggacacggt ggcttagt                                                  18
```